United States Patent [19]

Seton

[11] Patent Number: 5,299,563
[45] Date of Patent: Apr. 5, 1994

[54] METHOD OF USING A SURGICAL RETRACTOR

[76] Inventor: Joseph Z. Seton, Trinity Pass, Pound Ridge, N.Y. 10518

[21] Appl. No.: 922,832

[22] Filed: Jul. 31, 1992

[51] Int. Cl.⁵ .............................................. A61B 17/02
[52] U.S. Cl. ........................................ 128/20; 128/898
[58] Field of Search ........................ 128/3, 20, 898; 606/198

[56] References Cited

U.S. PATENT DOCUMENTS

| | | |
|---|---|---|
| 1,375,445 | 4/1921 | Crossley . |
| 1,400,616 | 12/1921 | McCrory et al. . |
| 1,747,799 | 2/1930 | Straus . |
| 2,541,516 | 2/1951 | Ivory et al. ............................ 128/20 |
| 2,564,118 | 8/1951 | Mahorner ............................. 128/20 |
| 3,168,093 | 2/1965 | Gauthier ............................... 128/20 |
| 3,221,743 | 12/1965 | Thompson ........................... 128/303 |
| 3,384,077 | 5/1968 | Gauthier ............................... 128/20 |
| 3,522,799 | 8/1970 | Gauthier ............................... 128/20 |
| 3,572,326 | 3/1971 | Jensen .................................. 128/20 |
| 3,749,088 | 7/1973 | Kohlmann ........................... 128/20 |
| 3,776,240 | 12/1973 | Woodson ............................. 128/361 |
| 3,965,890 | 6/1976 | Gauthier ............................... 128/20 |
| 3,998,217 | 12/1976 | Trumbull et al. ................... 128/20 |
| 4,257,406 | 3/1981 | Schenk ................................ 128/20 |
| 4,337,763 | 7/1982 | Petrassevich ...................... 128/20 |
| 4,344,420 | 8/1982 | Forder ................................. 128/20 |
| 4,412,532 | 11/1983 | Anthony ............................. 128/20 |
| 4,610,243 | 9/1986 | Ray ...................................... 128/20 |
| 4,784,150 | 11/1988 | Voorhies ............................. 128/664 |
| 4,817,587 | 4/1989 | Janese ................................. 128/20 |
| 4,834,067 | 5/1989 | Block .................................. 128/4 |
| 4,887,756 | 12/1989 | Puchy .................................. 227/19 |
| 5,052,374 | 10/1991 | Alvarez-Jacinto ................. 128/20 |

OTHER PUBLICATIONS

Seton, Dr. Joseph "Disclosure Document-Seton Hernia Retractor", Nov. 26, 1991.
Welsh, Inguinal Hernia Repair, etc. Apr. 1, 1974 pp. 49–56.
Blakemore, Shearburn et al., Shouldice Repair for Inguinal Hernia, Aug. 1969, Surgery vol. 66, No. 2, pp. 450–459.
Wantz, Canadian Repair of Inguinal Hernia, in Hernia, ed. Nyhus et al., pp. 236–248.
Skandalakis et al., Surgical Anatomy of the Inguinal Area Parts II, Contemporary Surgery vol. 38, Jan. 1991, pp. 20–37.

Primary Examiner—Richard J. Apley
Assistant Examiner—Donna L. Maraglio
Attorney, Agent, or Firm—Kuhn and Muller

[57] ABSTRACT

A method of surgical repair using a surgical retractor device is provided for opening a shallow surgical hernia site, wherein opposite frame members are provided, each of the opposite pairs having either shallow pointed tip hooks or opposite rounded corner blades. A first plurality of pointed tip hooks is movable in an axial direction toward or away from an opposing, stationary set of pointed tip hooks to facilitate axial movement of said first plurality of pointed tip hooks toward and away from said opposing stationary plurality of pointed tip hooks, by means of the movement of said first, movable plurality of pointed tip hooks on a main bar about parallel strut bars. The positioning of the retractor element renders the connection of the retractor irrotational within the surgical site.

2 Claims, 5 Drawing Sheets

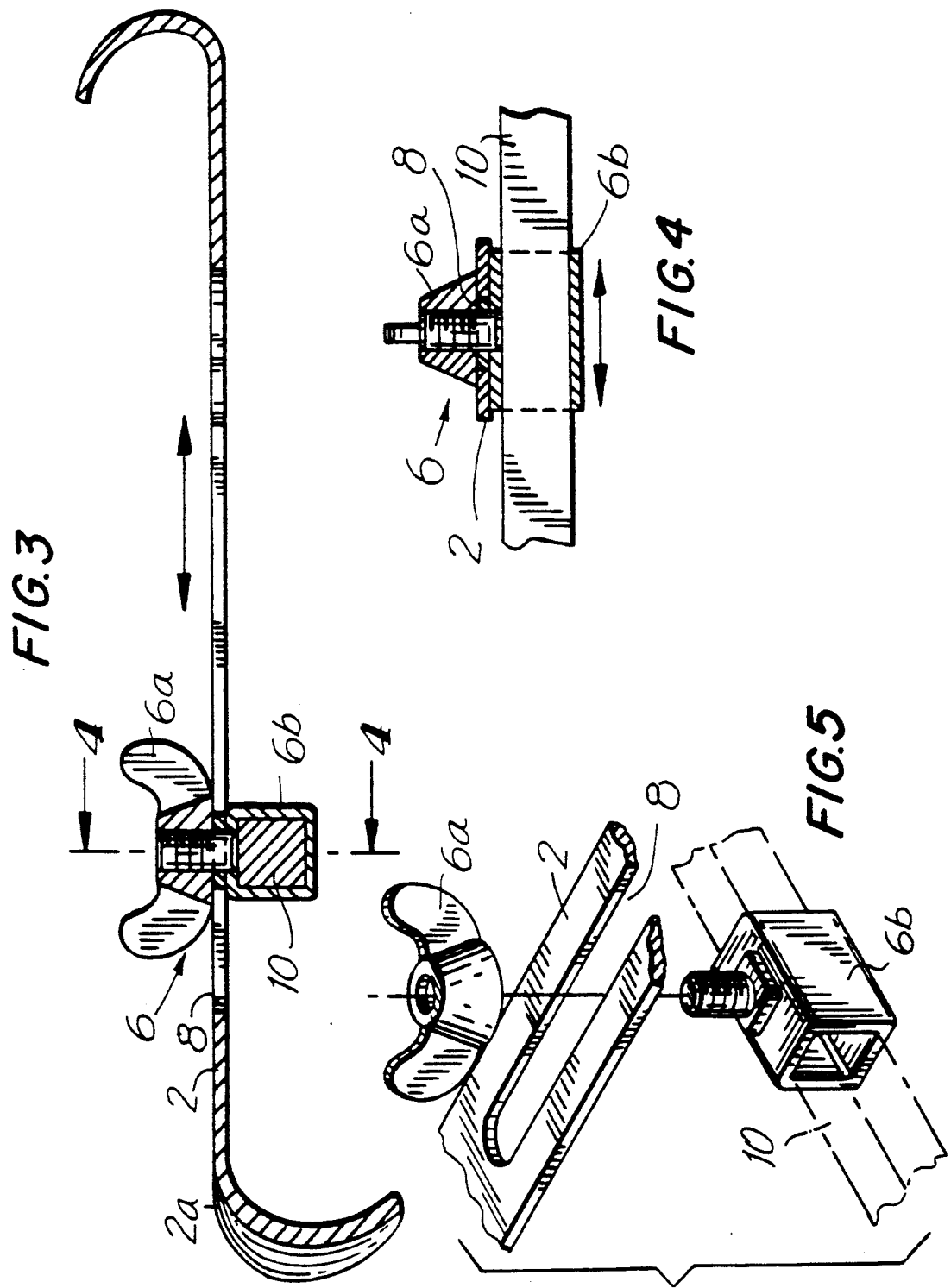

METHOD OF USING A SURGICAL RETRACTOR

This application relates to a Disclosure Document filed Nov. 26, 1991 entitled "Seton Hernia Retractor."

BACKGROUND OF THE INVENTION AND PRIOR ART

The present invention relates to a method of using a retractor device for the surgical repair of shallow body sites, such as inguinal, femoral, and incisional hernias., requiring a special stable retractor which is firmly, but removably fastened to the shallow surrounding tissues of the shallow incision.

Other shallow surgeries for which the present invention is applicable include neck surgeries, wherein shallow tissues such as the platysma muscles and sternocleidomastoid muscles must be held apart. The present invention may also be used in vascular surgeries, such as femoral bypass surgeries, laminectomies, wherein shallow erector-spinae muscles must be retracted, abdominal wall surgeries, thyroid surgeries and skin melanoma excisions.

The retractor includes an adjustable four sided frame with opposing pairs of frame members, each pair having different but cooperative holding elements. One pair of holding elements is for holding open the opposing skin corners of the incision from encroachments by fatty tissues, and the other pair of holding elements is for spreading open the incision and maintaining the fitting of the retractor in place at the incisional site without slippage or shifting. The former includes a pair of holding elements with two extension members with rounded corner blades for wrapping around and gently holding the skin corners apart.

The latter includes another pair of further holding elements, each further holding element including a plurality of pointed tip hooks for anchoring the retractor in place at the incisional site.

Each of the holding elements may be alternately attached to extension members which each have a slot axially extending for a portion of the length of the extension member to vary the distance of the respective holding elements from each other. The movement of one of the holding elements and extension members toward or away from another of the respective other holding elements and extension members thereto is accomplished by the axial movement of a wing nut within the axial slot, within the extension member of each holding element.

To insure stability of the present invention at a shallow surgical site, there is provided a four sided frame with two pairs of opposing generally linear frame elements, including a pair of generally linear parallel main bars, each main bar having two ends, and the pair of generally linear main bars connected at each end to respective ends of a pair of opposing generally linear strut bars holding the rounded corner blade holding elements. The generally linear main bars each have extending generally perpendicular therefrom the aforementioned plurality of pointed tip hooks for anchoring the retractor in place at the incisional site.

Because hernia surgery requires shallow incisions, it is important that the retractor be held in place without slippage or shifting during the surgery. Unlike deep incision conventional retractors, which have deep scoops for reaching down within the body to anchor the retractor in place around organs, tissue and fascia deep within the body, the hernia surgery incision is quite shallow, with very little tissue for anchoring the retractor in place. Therefore, the present retractor includes the aforementioned opposing pairs of pointed tip hooks which extend generally downward vertically, perpendicular to the plane of the major axis of the main bars of the retractor for a short distance, to limit the vertical distance of the frame from the anchored incisional site, so that the center of gravity of the retractor frame is close to the tissue walls against which the pointed tip hooks contact. These pointed tip hooks curve inward toward the incised walls, so that the hooks can contact and engage the shallow hernia incisional tissues and anchor the retractor in place at the surgical incision without slippage or shifting.

Shallow hernia surgeries are discussed in general in scholarly scientific texts, such as Welsh,"Inguinal hernia repair: a contemporary approach to a common procedure," MODERN MEDICINE, Apr. 1, 1974, pp. 49-54, New York Times Media Company, Inc.; Blakemore, "Should ice repair for inguinal hernia," SURGERY, Aug. 1969, Vol. 66, No. 2, pp. 450-459; Wantz, "The Canadian Repair of Inguinal Hernia," HERNIA, Third Edition, Chapter 12, ed. Nyhus, J. B. Lippincott Company, pp 236-248; and Skandalakis et al, "The Surgical Anatomy of the Inguinal Area - Part I, CONTEMPORARY SURGERY, Vol. 38, Jan. 1991, pp. 20-37.

The unpatented prior art includes the Applicant's use of a Vietlander retractor tool, which surgical tool traditionally includes two handles movable about a common hinge, such that manual exertion of force in the scissors-type handles causes opposite teeth-like end portions to hold opposite sites of an incision open during surgery. However, the repeated use of a Vietlander retractor demonstrated that other retractors and assistants were necessary simultaneously, such as a Richardson retractor or a hernia hook, which retractors may be subject to slippage from a desired position at the surgical site.

Subsequent use of a Vietlander retractor in combination with a rounded bladder blade failed to make the incisional site any more stable to any significant decree.

Moreover, the repeated use of a three sided U-shaped Balfour type frame, failed to stabilize the incisional site either. In the Balfour U-shaped frame, there is provided a pair of opposing, parallel frame elements, connected at one end by a third, perpendicular frame member. The two opposing frame members of the Balfour three sided frame each have extending perpendicularly downward further U-shaped retracting elements with rounded edges. These further U-shaped elements may stabilize deep, non-shallow surgical sites, such as abdominal surgeries, because the further U-shaped elements can anchor the prior art retractor in place by pressing against deep organs and tissues.

However, the use of such a Balfour type frame, with a rounded bladder blade extending from the third, perpendicular frame element, failed to significantly stabilize this prior art retractor in place, resulting in loosening of the retractor from shallow surgical sites without other -manual restricting measures.

Prior surgical retractor patents do not achieve the stability of the present invention, which prior art patents include U.S. Pat. No. 1,400,616 of McCrory and Person, as well as U.S. Pat. No. 2,564,118 of Mahorner, which both describe the use of teeth-like retractors on frames. U.S. Pat. Nos. 3,168,093 of Gauthier, 3,965,890 also of Gauthier, and 4,344,420 of Forder are examples of patents that disclose the use of rounded elements mounted on frames. Other U.S. Pat. Nos., such as Strauss, Pat. No. 1,747,799, Crossley, Pat. No. 1,375,445, Thompson, Pat. No. 3,221,743 and Jensen, Pat. No. 3,572,326, relate to adjustable frames and retractor elements.

U.S. Pat. No. 5,052,374 of Alvarez-Jacinto discloses a hernia retractor in an elliptical frame for shallow hernia surgeries. However, the Alvarez-jacinto device uses spring-loaded "clothes pin" types of holders to pinch and grip incised tissues, utilizing complicated mechanisms which may possibly cause ischemia and interfere with blood-flow within the squeezed portions of the incised tissues. In addition, since each pincer tool of Alvarez-Jacinto must be individually applied, the retractor may slip during installation.

While the Mahorner device has teeth-like retractors, and the Gauthier devices show scoop-like retractor blades, none of these prior art patents describe in symmetrical combination opposing pairs of shallow holding elements with different but cooperating-features to open and stabilize a shallow incisional site. None of the prior art patents other than Alvarez-Jacinto teach in combination a retractor applicable for shallow hernia surgery of approximately ¾" to several inches deep, requiring both a shallow support and stable tissue separation.

For example, while the McCrory and Person retractor utilizes finger hooks, the finger hooks extend from a non-adjustable elliptical frame having a pair of opposing convex ends, adjacent to a pair of concave sides to f it the contour of the abdomen. The drawback to the McCrory and Person device in shallow surgeries is that the "window" of the open surgical site cannot be quickly closed, as is necessary in shallow surgeries where overlaying tissues and musculatures are incrementally sutured in stages. Moreover, while the Mahorner thyroidectomy retractor includes two opposing sets of prongs, the prongs are located upon the apex of two generally upside down U-shaped bars, to drape over and fit the convex configuration of the neck being incised. The Mahorner device does not have rounded blades to assist in anchoring the device, by retracting fatty tissues at the corners of a shallow surgical site, such as a hernia surgery site.

Other retractor instruments are described in U.S. Pat. Nos. 4,412,532 of Anthony, 3,776,240 of Woodson, 3,749,088 of Kohlmann, 4,257,406 of Schenk, 4,337,763 of Petrassevich, 4,784,150 of Voorhies, 4,887,756 of Puchy, 4,610,243 of Ray, and 4,834,067 of Block.

Many of the aforementioned patents are for retractors for deeper surgery, where the holding elements can grab onto deeper tissues and elements, or have complicated holding mechanisms for shallow surgeries, such as eye surgery.

The bladder type scoop-like retractor blades of Gauthier hold skin flaps apart, but do not anchor in place in the same manner as the present invention. The present invention uses rounded bladder type scoop-like blades to hold back movable corner fatty tissues, which must be held back from retreating back towards the surgical site. If so, intruding fatty tissues can obstruct the vision of the surgeon.

Moreover, the prior patents do not describe a retractor which in combination both holds back fatty tissue while stabilizing the retractor within a shallow surgical site, to keep the retractor from slipping and therefore loosening or springing out of its site during surgery.

In addition, the use of the bladder type scoop blades in the present invention isolates the site from migrating fatty tissues, which are much more mobile than deeper internal organs in deeper non-hernia type surgeries, while the retractor is held in place by opposing pluralities of pointed tip hooks engaging the incised tissues.

Furthermore, the prior art patents do not describe a retractor which facilitates the unique suturing of a hernia surgery, which is generally done by repeated suturing of overlapping layers of tissue like flaps of a double-breasted suit, wherein the skin and tissue flaps keep getting smaller until the surgical site is closed.

For example, in shallow hernia surgeries, it is necessary to constantly and incrementally open and close the opening of the visual "window" of the retractor frame in width with adjustment type fasteners until the outer stitching is complete. A typical example of this type of surgery or technique is noted in the medical references as a "should ice Canadian hernia surgery." With the present invention, post incisional stitching is accomplished by incremental reduction in size of the open "window" of the frame, wherein the parallel main bars with the pointed tip hooks may be moved closer together by slidably moving one of the main bars with the pointed tip hooks along the axis of the parallel strut bars toward the other main bar. The gradual closing of the wound is accomplished by the aforementioned techniques, which require a tension-free wound to prevent surgical sutures from ripping or breaking from the wound site.

Optionally the pointed tip hooks may be permanently affixed to the main bars of the present invention, or the pointed tip hooks may be formed integrally with extension members having slots extending axially therein, to permit the adjustable placement of the pointed tip hooks with respect to each other when inserted within the body being incised.

OBJECTS AND GENERAL DESCRIPTION

It is an object of the present invention to provide a method of surgical using a shallow surgical retractor which avoids the disadvantages of the prior art and which allows the surgical retractor to be firmly held in place within shallow surgical tissue without shifting or slippage, thereby providing a safeguard against inadvertent detachment of the surgical retractor from the incisional site.

According to the invention, this object is attained with the device set out herein, in that a method of shallow surgical repair using a frame with opposite pairs of frame members is provided, with each pair having opposing, cooperating retracting elements with different retracting functions. One pair of retracting elements serves to gently hold open the surgical flaps of fatty tissue and skin at the top and bottom corners of the incision, while the opposing pairs of retracting elements contact and engage the median sides of the surgical incision to anchor the retractor in place.

The present invention facilitates the holding apart of corner flaps of skin and prevents fatty tissues from migrating into the site of the incision, thereby visually impairing the view of the surgeon and encumbering the incisional site with unwanted tissues. This permits the incision to be kept open during the course of a shallow surgery, such as hernia surgery.

A further object of the present invention is to provide a mechanism for reducing the opening of the incision site as the incision is sewn together with stitches as surgery proceeds.

This object is accomplished by utilizing the adjustability of the position of the opposite main bars supporting holding elements with extension members having pointed tip hooks. One of the holding elements with pointed tip hooks moves closer to the other stationary holding element, also having pointed tip hooks, until the skin and tissue flaps are adjacent to each other for final stitching. This feature is important because in a hernia or other shallow surgery it is helpful to gradually close the site, while maintaining retractor stability and the visual operating window, since the shallow tissues beneath the surgical site are quite moveable, because they are close to the surface of the body.

To achieve these objects, the present method utilizes a surgical retractor including a pair of horizontally spaced substantially linear frame structural members spaced in an adjustable rectangular shape, the frame members being spaced apart and each having one of opposite holding elements, such as the aforementioned curved corner blades to hold open the skin corners or the aforementioned pluralities of pointed tip hooks to firmly hold the surgical retractor in place in a shallow surgical site and spread the wound open. The vertical depth of the pointed tip hooks depends on factors such as the mass of the incised material and the spacing of the incision to the depth of the hernia site. However, the vertical distance of the pointed tip hooks and of the rounded corner blades below the frame itself is short, depending upon body size measurements. As a result, the center of gravity of the frame is close to the surface of the tissues being contacted by the pointed tip hooks, thereby further stabilizing the retractor in place at the incisional site.

Moreover, the holding elements are arranged so that they define a plurality of opposite holding elements, including the opposing set of main bars having pointed tip hooks, such that one plurality of hooks adjustably closes incrementally towards the opposing, other plurality of hooks, as the surgery is being finished and width of the surgical incision decreases.

The opposite structural members, namely a pair of strut bars and a pair of main bars, are generally straight and parallel to each other. In the preferred embodiment, as noted before, there are a pair of two strut bars adjacent to a pair of two main bars, and one of the main bars is movable towards the other main bar as it slides axially along both of the parallel strut bars when loosened from a tightened position.

Furthermore, the rounded bladder-type corner blades provide a rounded surface with which the fatty tissue and flaps of the corners of the incised skin may be separated without irritation to the fatty tissues and skin.

The method of using a present surgical retractor allows for adequate exposure of the incised tissues, which makes for a safer and more expeditious operation. In the past generally more than one separate, manually held retractor was required for exposure as well as an assistant to constantly hold it, reposition it, etc, or else the retractor had complicated holding mechanisms. With the present method of using a retractor there is no need for an assistant to hold the retractor, and no further possibility for an assistant's fatigue. Therefore, the retractor remains stationary during shallow surgery.

DETAILED DESCRIPTION OF THE DRAWINGS:

The invention will now be described, by way of example, with reference to the accompanying drawings in which:

FIG. 3 is a side elevational view in partial section of a scoop corner blade portion of the device.

FIG. 4 is a close up sectional view of a scoop portion fastener of the device along line 3—3, along line 4—4 of FIG. 3.

FIG. 5 is an exploded perspective closeup view of the scoop portion fastener as shown in FIG. 3.

DESCRIPTION OF THE PREFERRED EMBODIMENT

Figure 1:
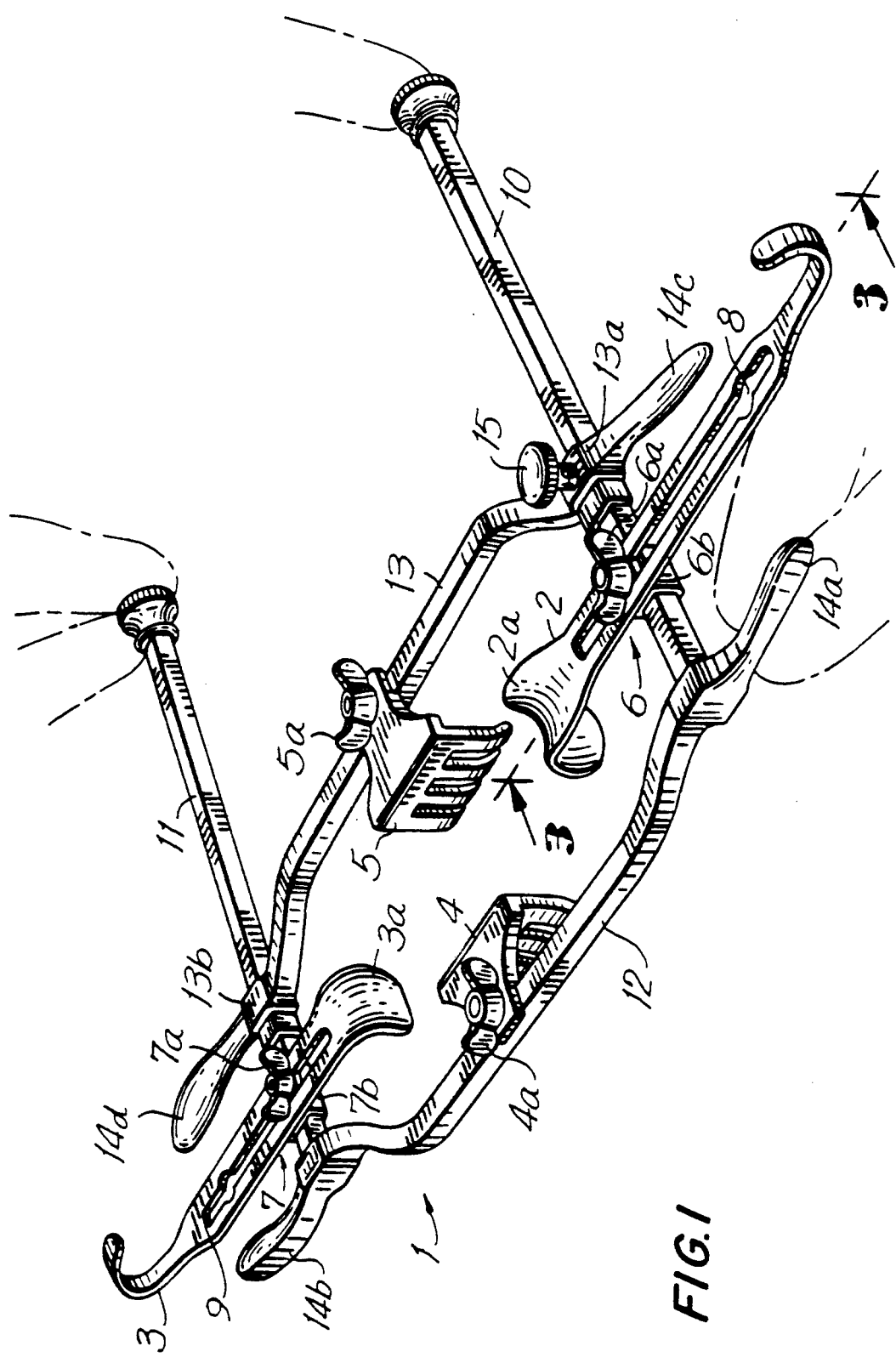
FIG. 1 is a perspective three-dimensional view of the device in accordance with the invention.
Figure 2:
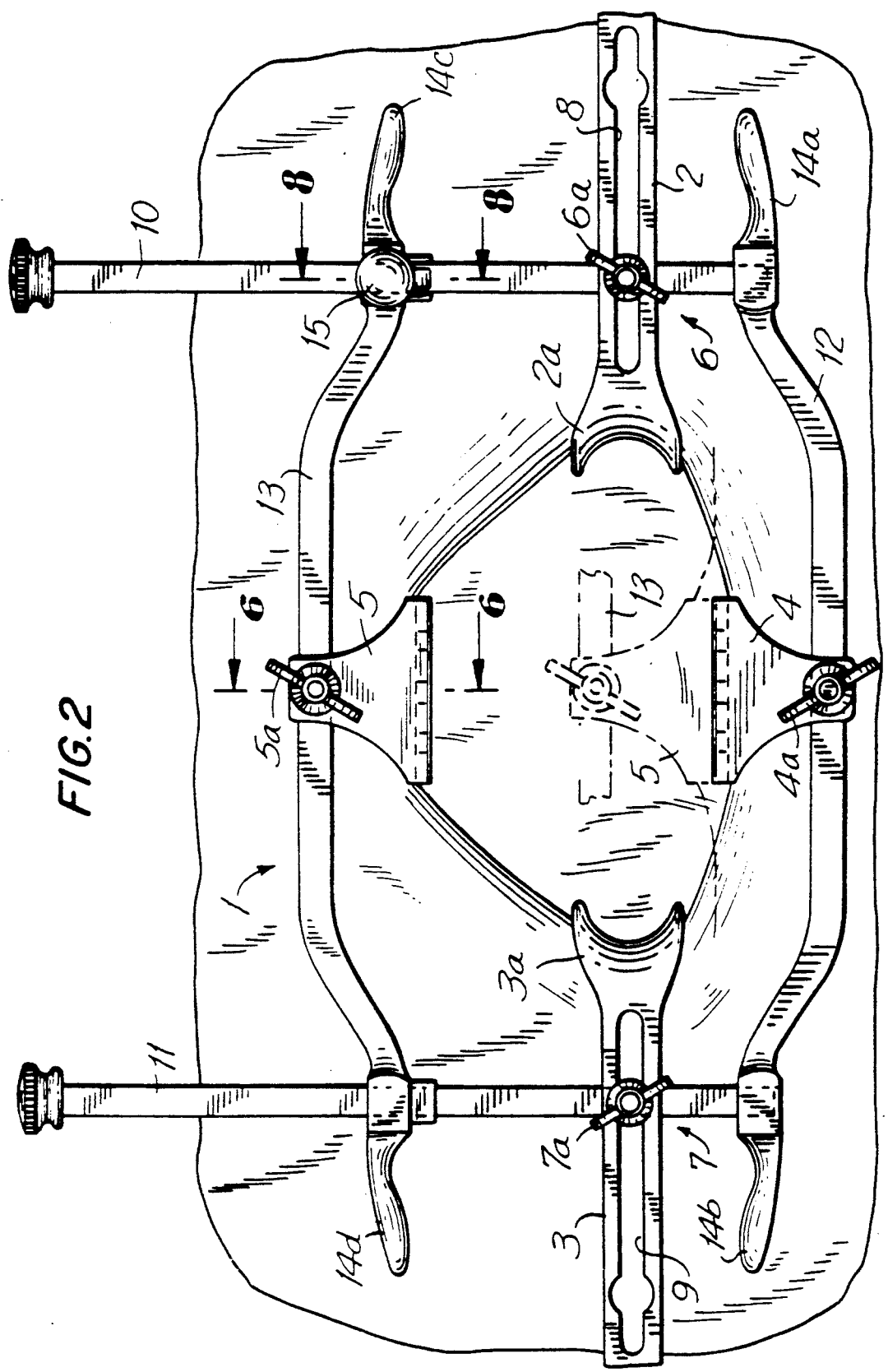
FIG. 2 is a top plan view showing the retractor in place in an incision.
Figure 7:
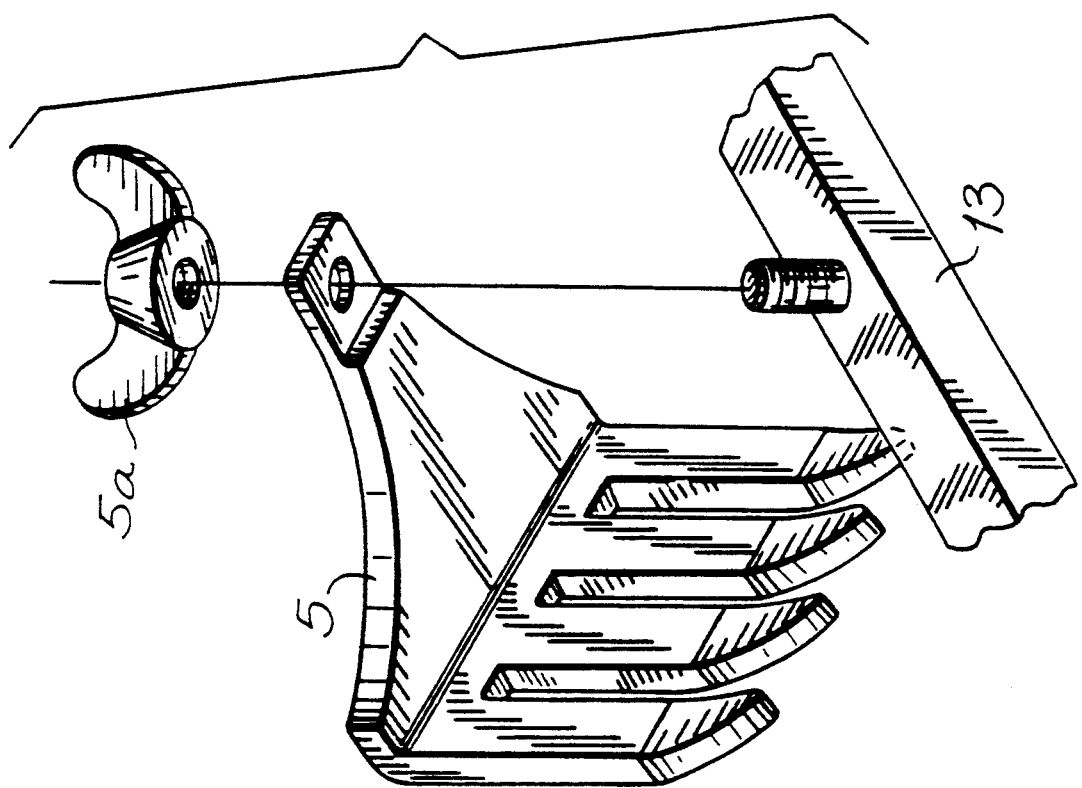
FIG. 7 is an exploded bottom closeup view in perspective of the pointed tip hook member of FIG. 6.
Figure 6:
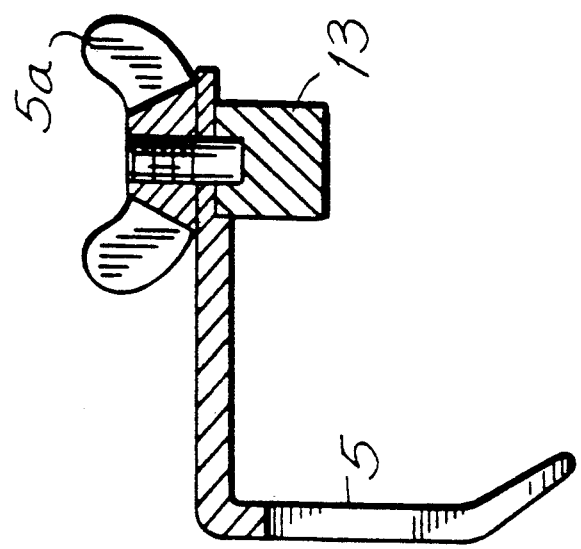
FIG. 6 is a close up partial sectional side elevational view of a pointed tip hook member of the device.

As illustrated in FIGS. 1-9 of the drawings, reference numeral 1 generally designates the hernia surgery retractor in accordance with the method of shallow surgical repair of the present invention. The retractor 1 includes two pairs of opposite, parallel bars, including strut bars 10 and 11 and main bars 12 and 13. The strut bars 10 and 11 have a slidable wing nut attachments 6 and 7, including wing nut 6a and wing receptacle 6b, as well as wing nut 7a and wing receptacle 7b such that the wing receptacles 6b and 7b are slidable along the outer surface of strut bars 10 or 11 respectively, for moving the position of rounded corner blade extension members 2 and 3 respectively, to a desired position along an axis perpendicular to strut bars 10 and 11. The wing nut attachments 6 and 7 position the rounded corner blades 2a and 3a of the corner blade extension members 2 and 3 along opposite corners of the skin flaps at the top and bottom of a linear surgical incision.

To hold the hernia surgical retractor in place, main bars 12 and 13 each contain respective pluralities 4 and 5 of pointed tip hooks, which pluralities of hooks 4 and 5 are capable of contacting and closely engaging into the left and right median side portions of the surgical incision, to hold the incisional retractor in place in the shallow surgical site without slippage. The plurality 5 of pointed tip hooks is movable about main bar 13 toward plurality 4 of pointed tip hooks supported by stationary main bar 12, to alternately and sequentially spread apart, hold open and move the incised tissues together during the course of the shallow surgery. It is important that the pointed tip hooks extend down perpendicular to the axis of the main bars 12 and 13 and then curve outward from the center of retractor 1 to contact and engage the incised tissues in the shallow incision.

The pluralities 4 and 5 of pointed tip hooks are conventionally attached to respective main bars 12 and 13 by wing nuts 4a and 5a.

The opposite ends of main bars 12 and 13 have opposing pairs of handles 14a, 14b, 14c and 14d for easy placement and removal of the surgical retractor in place on the surgical site.

Retractor 1 retracts the incised shallow tissues, such as fat, skin, fascia and muscles of the inguinal canal, so as to expose the underlying tissues requiring repair. Retractor 1 accomplishes retraction in the shallow surgical site without slippage or shifting, which slippage or shifting would ordinarily occur in conventional retractors not having complicated anchoring means. Conventional surgical retractors generally are held in place by deep anchoring of the holding elements against the tissues deep within the body, or by complicated holding mechanisms. In shallow surgery, such as hernia surgery, where the incision may be only in depth up to several inches deep, there is very little tissue to anchor and hold the retractor in place. Therefore retractor 1 has the configuration of a four sided frame with opposing sets 2,3 and 4,5 of holding elements, namely, the plurality of pointed tip hooks 4 and 5 at the sides of the surgical site to anchor the retractor 1 in place, in conjunction with opposing pairs of rounded corner blades 2a and 3a to keep fatty tissues away from the surgical site.

The incised tissue corner flaps are held in place by the rounded corner blades 2a and 3a of the corner blade extension members 2 and 3, which corner blades 2a and 3a are placed at the top and bottom corners of the surgical site where the migrating fatty tissues are most apt to invade the surgical site. The isolation of the fatty tissue from the surgical opening is achieved by moving the skin flaps away from each other, by placement of the rounded corner blades 2a and 3a of the extension members 2 and 3 away from each other. Positioning of the corner blade extension members 2 and 3 is accomplished by virtue of the lengthwise axial movement of the holding extension members 2 and 3 along their inner slots 8 and 9 about the wing nut attachments 6 and 7, which wing nut attachments 6 and 7 are also slidable along strut bars 10 and 11 in an axis perpendicular to the surgical incision, until the rounded corner blades 2a and 3a are in place at the top and bottom corners of the surgical incision.

The retractor 1 of the present invention is preferably made of stainless steel and rectangular in shape, although other geometric configurations are possible, so long as the retractor 1 is generally four sided. When it is opened for shallow hernia surgery, the retractor 1 is sized approximately 13 cm by 15 cm, describing preferably a rectangle. Removably attached to generally linear main bars 12 and 13 are the teeth of the pluralities 4 and 5 of pointed tip hooks, similar to those found on what is referred to as a Vietlander retractor. The pluralities 4 and 5 of pointed tip hooks contact and engage into each of the lateral sides of the incised wound, approximately at a median mid-point of either side of the wound's longitudinal axis, thereby allowing the skin and fascia, i.e. the external oblique, to be retracted.

The teeth of the pluralities 4 and 5 of pointed tip hooks slightly penetrate the shallow tissues of the incisional site and consequently prevent the retractor 1 from slipping out of position, and in combination with the opposing set of rounded corner blades, thereby make the retractor 1 irrotational within the surgical site.

The method of shallow surgical repair using retractor 1 of the present invention more precisely and adequately retracts the tissues involved in the repair of an inguinal, femoral or incisional hernia. By using the present retractor 1 there is no need for a multiplicity of retractors or complicated holding mechanisms. With the retractor 1, a hernia operation can be done with a surgeon and a scrub nurse only.

In a preferred further embodiment, one for which the surgical site has a larger or smaller than usual initial opening with varied vertical depth to the point of contact for the pluralities 4 and 5 of pointed tip hooks, the surgeon is able to alter the depth of the pointed tip hooks, by means of a removable attachment with adjustably sized pointed tip hooks. In this further embodiment, the pluralities 4 and 5 of pointed tip hooks and rounded corner blades 2 and 3 can be interchangeable with other sized sets of hooks, for different body surgical depths. Therefore the variation in depths of the pointed tip hooks and corner blades accommodate different patient body sizes, i.e., thin, medium and obese.

In use, the opposite pairs of strut bars 10 and 11 and main bars 12 and 13 are spread apart from each other, generally leaving an open rectangular surgical site. However, because of the necessity of gradually closing a hernia site with stitching, it is necessary to incrementally close the hernia site. Therefore, the retractor 1 provides that, when closing the hernia site, the plurality 5, of pointed tip hooks is gradually moved towards plurality 4 of pointed tip hooks by movement of the main bar 13 towards main bar 12, about linear strut bars 10 and 11.

Therefore, to close the visual window of the hernia site, main bar 13 may be quickly and efficiently movable towards main bar 12 along the longitudinal axis' of strut bars 10 and 11.

Handles 14a and 14b attach to stationary main bar 12 and handles 14c and 14d attach to movable main bar 13. Adjacent to handles 14c and 14d of main bar 13, the end portions 13a and 13b of main bar 13 are hollow, so that main bar 13 slidably moves about struts 10 and 11 toward main bar 12 when further tightening fastener 15 is loosened incrementally as the surgeon completes the surgery and reduces the size of the frame of the retractor 1. Therefore, the retractor may be reduced in size as surgery progresses.

The method of using retractor 1 is useful in shallow hernia incisions where the tissues may collapse inward towards each other, thereby requiring a shallow support to maintain the hernia retractor in place.

To position the rounded blades 2a and 3a in place at the top and bottom corners of the incisional site, slots 8 and 9 of the corner blade extension members 2 and 3 are so formed so that the extension members 2 and 3 move in and out in one direction, longitudinally and axially parallel to the main bars 12 and 13 and perpendicular to the strut bars 10 and 11 upon which extension members 2 and 3 move back and forth toward each other until the rounded blades 2a and 3a are in place at the top and bottom of the corners of wound site to prevent migration of fatty tissues into the incisional site.

Figure 9:
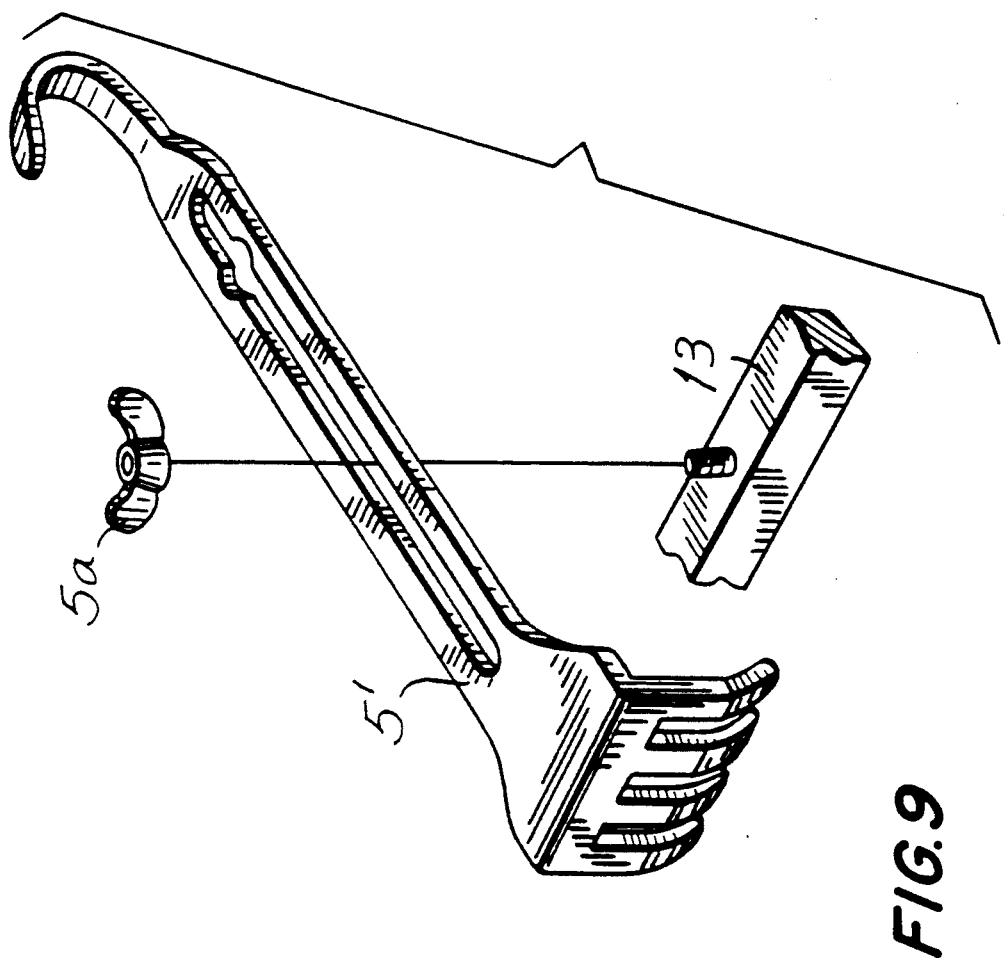
FIG. 9 is an exploded perspective view of an adjustable pointed tip hook member.
Figure 8:
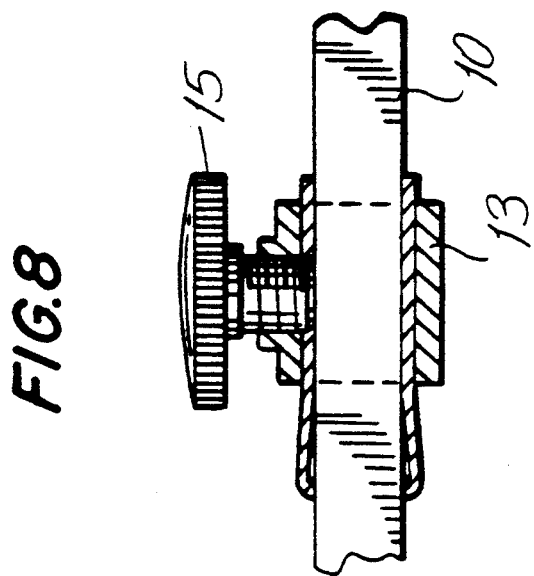
FIG. 8 is a closeup view of the fastener for the strut bar of the device.

Likewise, alternative sets of pointed tip hooks, such as pointed tip hook set 5' of FIG. 9, may have extension members with axial slots for positioning the sets of pointed tip hooks in place at the surgical site.

To summarize, in the preferred embodiment, the method of shallow surgical repair include surgical retractor 1 which has an adjustable rectangular frame. The main bars 12 and 13, in opposition, have the pluralities 4 and 5 of teeth-like pointed tip hooks mounted thereon, for holding the surgical retractor in place, during the opening of the surgical site, the progress of the surgery itself and the closing of the incisional site.

Moreover, in shallow surgical operations, the surgical site is quickly and incrementally closed by moving plurality 5 of pointed tip hooks and main bar 13 towards opposite plurality 4 of pointed tip hooks and stationary main bar 12, during the opening and the closing of the site of the hernia surgery.

It is to be noted that other variations may be made to the present invention, without departing from the spirit and scope of the present invention, as stated in the appended claims.

I claim:

1. A method of surgical repair at a shallow surgical site using a retractor device wherein the retractor device comprises a) a frame including first and second substantially parallel, spaced strut bars, each having first and second ends, said first strut bar having a first rounded holding element attached thereto and said second strut bar having a second rounded holding element attached thereto, b) a first main bar disposed generally perpendicular to said first and second strut bars, and connected to said first ends of said first and second strut bars, said first main bar having a first hooked holding element being attached thereto at a position between said first and second strut bars, and c) a second main bar disposed generally parallel to said first main bar and generally perpendicular to said first and second strut bars, said second main bar being slidably attached to said first and second strut bars for movement toward and away from said first main bar, and having a second hooked holding element attached thereto at a position between said first and second strut bars, wherein the method comprises the steps of:

forming a surgical incision at the shallow surgical site, the incision having a first end, a second end, a first side, and a second side;

placing the first and second hooked holding elements into the incision in engagement with the first and second sides, respectively, of the incision;

anchoring the first and second rounded holding elements in place against the first and second ends, respectively, of the incision;

spreading open the incision to expose the surgical site by sliding the second main bar along the first and second strut bars in a direction away from the first main bar, thereby causing the first and second hooked holding elements to spread the first and second sides of the incision apart;

performing the necessary surgical repair at the surgical site;

incrementally reducing an opening of the incision while suturing the incision by gradually sliding the second main bar along the first and second strut bars and toward the first main bar so that the second hooked holding element gradually moves closer toward the first hooked holding element, until the first and second sides of the incision are adjacent to each other; and removing the retractor device and completing suturing of the incision.

2. The method of claim 1, wherein the retractor device further includes a single tightening means, disposed on the second main bar, for selective engagement with the first strut bar to fix the position of the second main bar relative to the first and second strut bars, and wherein the method further comprises:

tightening the single tightening means after the second main bar is moved away from the first main bar to spread open the incision; and loosening the single tightening means to enable movement of the second main bar gradually toward the first main bar during suturing of the incision.

* * * * *